United States Patent [19]

Kay

[11] 4,011,325
[45] Mar. 8, 1977

[54] IMIDAZOPYRIMIDINES USEFUL AS AGRICULTURAL AND HORTICULTURAL FUNGICIDES

[75] Inventor: Ian Trevor Kay, Wokingham, England

[73] Assignee: Imperial Chemical Industries Limited, London, England

[22] Filed: Mar. 27, 1975

[21] Appl. No.: 562,423

[30] Foreign Application Priority Data

Mar. 27, 1974 United Kingdom .............. 13563/74

[52] U.S. Cl. ........................ 424/251; 260/256.4 F
[51] Int. Cl.² ....................................... C07D 487/04
[58] Field of Search .............. 260/256.4 F; 424/251

[56] References Cited

UNITED STATES PATENTS 3,769,288   11/1973   Stähle et al. ................. 260/256.4 F
3,816,422    6/1974   Stähle et al. ................. 260/256.4 F

OTHER PUBLICATIONS

Prokof'ev, et al., "Chemical Abstracts," vol. 49 (1955), col. 9661b.

Lucas, *Organic Chemistry*, Sec. Ed., 1953, American Book Company, New York, pp. 211–220.

*Primary Examiner*—Donald G. Daus
*Assistant Examiner*—James H. Turnipseed
*Attorney, Agent, or Firm*—Cushman, Darby & Cushman

[57] ABSTRACT

A compound of the formula:

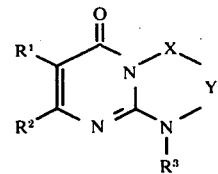

wherein $R^1$, $R^2$ and $R^3$ are alkyl groups of up to six carbon atoms, and X and Y are independently selected from the group consisting of carbonyl, hydroxymethylene, an ether of hydroxymethylene and an ester of hydroxymethylene. These compounds are useful as agricultural and horticultural fungicides.

8 Claims, No Drawings

IMIDAZOPYRIMIDINES USEFUL AS AGRICULTURAL AND HORTICULTURAL FUNGICIDES

This invention relates to novel heterocyclic compounds useful as fungicides in agriculture and horticulture.

Accordingly, the present invention provides novel heterocyclic compounds of formula:

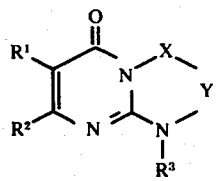

wherein $R^1$, $R^2$ and $R^3$ are alkyl groups comprising up to six carbon atoms and X and Y are independently selected from carbonyl, hydroxymethylene, an ether of hydroxymethylene and an ester of hydroxymethylene.

Preferred compounds are those wherein $R^1$ is n-butyl, $R^2$ is methyl and $R^3$ is ethyl.

Particular compounds according to the invention include those listed in Table I below, wherein the meanings of $R^1$, $R^2$, $R^3$, X and Y are set out together with a melting point for each compound.

pounds wherein the -X-Y- fragment represents the group:

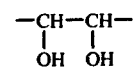

glyoxal may be used, and when the -X-Y- fragment represents the group:

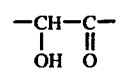

then glyoxalic acid may be used. If the treatment with glyoxal is carried in the presence of sulphuric acid and an alcohol of formula ROH (wherein R is lower alkyl) then a group of formula:

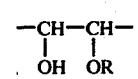

is formed. Also the product obtained by the treatment with glyoxal may be acylated to give rise to esters. Thus treatment with glyoxal followed by treatment with acetic anhydride gives rise to a compound wherein the -X - Y- fragment represents a group of formula:

TABLE I

| Compound No. | $R^1$ | $R^2$ | $R^3$ | X | Y | m.p. 0° C |
|---|---|---|---|---|---|---|
| 1 | n-C₄H₉ | CH₃ | C₂H₅ | CH—OH | CH—OH | 132 |
| 2 | n-C₄H₉ | CH₃ | C₂H₅ | CH—OH | C=O | 109 |
| 3 | n-C₄H₉ | CH₃ | C₂H₅ | CH—OH | CH—OC₂H₅ | 79 |
| 4* | n-C₄H₉ | CH₃ | C₂H₅ | CH—OCOCH₃ | CH—OCOCH₃ | — |

*This compound was obtained as an oil. The compounds were identified by infra-red and nuclear magnetic resonance spectroscopy and gave satisfactory elemental analyses.

The compounds of the invention may be obtained by treating a compound of formula:

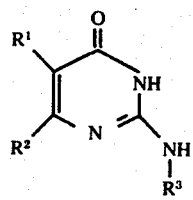

wherein $R^1$, $R^2$ and $R^3$ are as defined hereinbefore with a compound capable of generating the required -X-Y- fragment (either directly or indirectly). Thus for com-

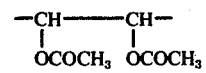

Thus once the -X - Y- fragment has been introduced into the molecule, derivatisation of the groups present may be carried out by conventional techniques.

The novel heterocyclic compounds are useful as fungicides for use in agriculture and horticulture, and are best utilised for this purpose in the form of a composition. In a further aspect the invention provides compositions for use in agriculture and horticulture comprising a compound of formula:

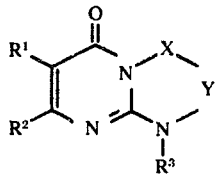

wherein $R^1$, $R^2$, $R^3$, X and Y have any of the meanings given hereinabove, in association with an agriculturally and horticulturally acceptable diluent or carrier.

The compositions may be in the form of dusting powders wherein the active ingredient is mixed with a solid diluent or carrier, for example, kaolin, bentonite, kieselguhr, or talc, or they may be in the form of granules, wherein the active ingredient is absorbed on a porous granular material, for example, pumice.

Alternatively, the compositions may be in the form of liquid preparations to be used as dips or sprays, which are generally aqueous dispersions or emulsions of the active ingredient in the presence of one or more known wetting agents, dispersing agents, or emulsifying agents. These compositions are prepared by dissolving the active ingredient in a suitable solvent, for example, a ketonic solvent such as diacetone alcohol, and adding the mixture so obtained to water which may contain one or more wetting, dispersing or emulsifying agents.

The compositions which are to be used in the form of aqueous dispersions or emulsions are generally supplied in the form of a concentrate containing a high proportion of the active ingredient, the said concentrate to be diluted with water before use. These concentrates are often required to withstand storage for prolonged periods and after such storage, to be capable of dilution with water in order to form aqueous preparations which remain homogeneous for a suffient time to enable them to be applied by conventional spray equipment. The concentrates may contain 10–85% by weight of the active ingredient. When diluted to form aqueous preparations such preparations may contain varying amounts of the active ingredient depending upon the purpose for which they are to be used.

For agricultural or horticultural purposes, aqueous preparations containing between 0.001% and 1.0% by weight of the active ingredient may be used.

The compositions of the present invention may, if desired, also comprise in addition to a compound of the present invention, at least one other biologically-active ingredient, for example, an insecticide or a fungicide.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are useful in the control of fungal diseases of plants, including, for example, the following:

*Phytophthora infestans* (blight of tomato)
*Plasmopara viticola* (*powdery mildew of vines*)
*Uncinula necator* (downy mildew of vines)
*Podosphaera leucotricha* (powdery mildew of apples)
*Sphaerotheca fuliginea* (powdery mildew of cucumbers)
*Erysyphe graminis* (powdery mildew of wheat/barley)

The invention is illustrated by the following examples.

EXAMPLE 1

This Example illustrates the preparation of 6-n-butyl-2,3-dihydroxy-1-ethyl-7-methyl-5-oxo-2,3-dihydroimidazo [1,2-a] pyrimidine (Compound No. 1, Table 1) having the formula:

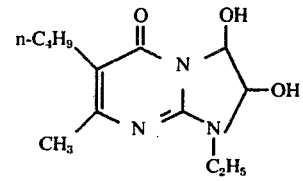

A mixture of 5-n-butyl-2-ethylamino-4-hydroxy-6-methylpyrimidine (4.30 g.), glyoxal monohydrate (90%, 1.70 g.) and methanol (50 ml.) was heated together at reflux temperature for 90 minutes, after which the methanol was removed by evaporation under reduced pressure. The residual oil crystallised on standing and was recrystallised from a mixture of dichloromethane and n-hexane to yield the product, melting point 132° C.

$C_{13}H_{23}N_3O_3$ requires C,58.4; H,7.87; N,15.70% found C,57.96, H,7.79; N,15.53%.

EXAMPLE 2

This Example illustrates the preparation of 6-n-butyl-2,5-dioxo-1-ethyl-3-hydroxy-7-methyl-2,3-dihydroimidazo [1,2-a] pyrimidine (Compound no. 2 Table I) having the formula:

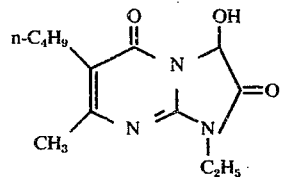

A mixture of 5-n-butyl-2-ethylamino-4-hydroxy-6-methyl-pyrimidine (3.80 g.), glyoxylic acid monohydrate (1.63 g.) and sodium dried toluene (50 ml.) was refluxed in an apparatus fitted with a Dean water separator until the theoretical amount of water had been collected. The solvent was removed by evaporation under reduced pressure and the residual oil, which crystallised out on standing was recrystallised from petroleum ether (boiling range 80° to 100° C.) to yield the required product, which had a melting point of 109° C.

$C_{13}H_{20}N_3O_3$ requires C, 58.70; H, 7.15; N, 15.85 found C, 58.44; H, 7.41; N, 15.75.

EXAMPLE 3

This Example illustrates the preparation of 6-n-butyl-2-ethoxy-1-ethyl-3-hydroxy-7-methyl-5-oxo-2,3,-dihydroimidazo [1,2-a] pyrimidine (Compound no. 3, Table I) having the formula:

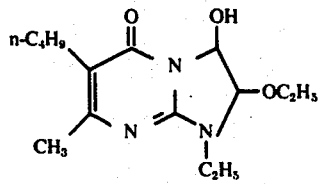

A mixture of 5-n-butyl-2-ethylamino-4-hydroxy-6-methyl-pyrimidine (2.15 g.) glyoxal monohydrate ethanol (50 ml.) was refluxed together for two hours after which the solvent was evaporated under reduced pressure. The residual oil was dissolved in dichloromethane (50 ml.) and the solution washed with aqueous sodium bicarbonate solution (15%) dried over anhydrous sodium sulphate. The dichloromethane was removed by evaporation under reduced pressure and the residue recrystallised from n-hexane to yield the required product, melting point 79° C.

$C_{15}H_{27}N_3O_3$ requires C,61.20; H, 8.16% found C,61.09; H, 8.59%.

EXAMPLE 4

This Example illustrates the preparation of 6-n-butyl-2,3-diacetoxy-1-ethyl-7-methyl-5-oxo-2,3-dihydroimidazo[1,2-a]pyrimidine (Compound no. 4, Table I) having the formula:

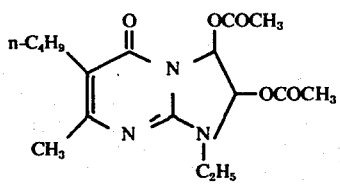

A mixture of 6-n-butyl-2,3-dihydroxy-1-ethyl-7-methyl-5-oxo-2,3-dihydroimidazo [1,2-a] pyrimidine (0.67 g.), acetic anhydride (0.78 g.) and pyridine (0.79 g.) was agitated for a period of 18 hours at the ambient temperature. To this mixture was added water (50 ml.) and dichloromethane (50 ml.) and after further agitation the dichloromethane solution was separated, washed with aqueous sodium bicarbonate solution, with dilute hydrochloric acid, and finally with water. The dichloro-methane solution was dried over anhydrous sodium sulphate and after stirring for 18 hours with activated charcoal and filtering, the solvent was removed from the filtrate by evaporation under reduced pressure to give an oil which was freed from any residual volatile component by warming to 30° C. for 3 hours under 0.01 mm. Hg. The viscous oil which remained was identified as the required product by infrared and nuclear magnetic resonance spectroscopy.

EXAMPLE 5

5 Parts by weight of Compound no. 1 of Table I were throughly mixed in a suitable mixer with 96 parts by weight of talc. There was thus obtained a dusting powder.

EXAMPLE 6

10 parts by weight of Compound no. 2 of Table I, 10 parts of an ethylene oxide-octylphenol condensate ("Lissapol" NX : Lissapol is a Trade Mark) and 80 parts by weight of diacetone alcohol were thoroughly mixed. There was thus obtained a concentrate which, on mixing with water, gave an aqueous dispersion suitable for application as a spray in the control of fungal pests of plants.

EXAMPLE 7

A granular composition was prepared by dissolving the active ingredient in a solvent, spraying the solution obtained on the granules of pumice and allowing the solvent to evaporate.

|  | % wt. |
|---|---|
| Compound No. 3 of Table I | 5 |
| Pumice Granules | 95 |
|  | 100 |

EXAMPLE 8

An aqueous dispersion formulation was prepared by mixing and grinding the ingredients recited below in the proportions stated.

|  | % wt. |
|---|---|
| Compound no. 4 of Table I | 40 |
| Calcium lignosulphonate | 10 |
| Water | 50 |
|  | 100 |

EXAMPLE 9

The compounds of this invention were tested against a variety of foliar fungal diseases of plants. The technique employed is to spray the foliage of the undiseased plants with a solution of the test compound and also to drench the soil in which the plants are growing with another solution of the same test compound. All solutions for spraying and drenching contained 0.02% of the test compound, except for compound no. 1 of Table I where the concentration was 0.01%. The plants were then infected with the disease it was desired to control and after a period of days, depending upon the particular disease, the extent of the disease was visually assessed. The results are given in Table 3 below, wherein the extent of the disease is given in the form of a grading as follows:

| Grading | Percentage Amount of Disease |
|---|---|
| 0 | 61 to 100 |
| 1 | 26 to 60 |
| 2 | 6 to 25 |
| 3 | 0 to 5 |

In Table 2 the disease is given in the first column, and in the second column is given the time which elapsed between infecting the plants and assessing the amount of disease.

TABLE 2

| Disease and Plant | Time Interval (days) | Disease Code Letter (Table 3) |
|---|---|---|
| Phytophthora infestans (tomato) | 3 | B |
| Plasmopara viticola (vine) | 7 | C |
| Podosphaera leucotricha (apple) | 10 | D |

TABLE 2-continued

| Disease and Plant | Time Interval (days) | Disease Code Letter (Table 3) |
|---|---|---|
| Uncinula necator (vine) | 10 | E |

TABLE 3

| Compound No. Table I. | Disease Code Letter Table 2 | | | |
|---|---|---|---|---|
| | B | C | D | E |
| 1 | 0 | 1 | 3 | 0 |
| 2 | 3 | 1 | 3 | 3 |
| 3 | — | 2 | 3 | 3 |
| 4 | 0 | 0 | 3 | 2 |

All the compounds were found to be active against *Sphaerotheca fuliginea* (powdery mildew of cucumber) and *Erysyphe graminis* (powdery mildew of barley) in tests to determine the protectant activity of the compounds at a rate of 50 p.p.m.

I claim:

1. A compound of formula:

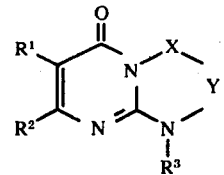

wherein $R^1$, $R^2$ and $R^3$ are alkyl groups of up to six carbon atoms, and X and Y are independently selected from the group consisting of carbonyl, hydroxymethylene, ethoxymethylene and acetoxymethylene.

2. A compound according to claim 1 wherein $R^1$ is n-butyl, $R^2$ is methyl and $R^3$ is ethyl.

3. A compound according to claim 1 said compound being:
6-n-butyl-2,3-dihydroxy-1-ethyl-7-methyl-5-oxo-2,3-dihydroimidazo [1,2-a] pyrimidine.

4. A compound according to claim 1, said compound being
6-n-butyl-2,5-dioxo-1-ethyl-3-hydroxy-7-methyl-2,3-dihydroimidazo [1,2-a] pyrimidine.

5. A compound according to claim 1, said compound being
6-n-butyl-2-ethoxy-1-ethyl-3-hydroxy-7-methyl-5-oxo-2,3-dihydroimidazo [1,2-a] pyrimidine.

6. A compound according to claim 1, said compound being
6-n-butyl-2,3-diacetoxy-1-ethyl-7-methyl-5-oxo-2,3-dihydroimidazo [1,2-a] pyrimidine.

7. A fungicidal compositions for use against fungal plant pests which comprises a fungicidally effective amount of a compound according to claim 1 in association with an agriculturally and horticulturally acceptable diluent.

8. A method of combatting fungal pests of plants which comprises contacting said plants with fungicidally effective amount of a composition according to claim 7.

* * * * *